(12) United States Patent
Storer et al.

(10) Patent No.: US 6,840,942 B2
(45) Date of Patent: Jan. 11, 2005

(54) PROSTHETIC IMPLANT CEMENT DEFLECTOR AND METHOD OF IMPLANTATION

(75) Inventors: John Andrew Storer, München (DE); Andrew John Timperley, St. Leonard's Exeter (GB)

(73) Assignee: Benoist Girard SAS (FR)

( * ) Notice: Subject to any disclaimer, the term of this patent is extended or adjusted under 35 U.S.C. 154(b) by 142 days.

(21) Appl. No.: 10/054,363

(22) Filed: Nov. 13, 2001

(65) Prior Publication Data

US 2002/0116005 A1 Aug. 22, 2002

(30) Foreign Application Priority Data

Nov. 15, 2000 (GB) .......................................... A00027893

(51) Int. Cl.[7] .............................................. A61B 17/58
(52) U.S. Cl. ......................................................... 606/92
(58) Field of Search ............................. 606/92, 93, 94; 623/908, 23.48

(56) References Cited

U.S. PATENT DOCUMENTS

| | | | |
|---|---|---|---|
| 5,156,606 A | * | 10/1992 | Chin ............................. 606/86 |
| 5,171,288 A | * | 12/1992 | Mikhail et al. ............... 623/23 |
| 5,197,990 A | | 3/1993 | Lawes et al. |
| 5,443,523 A | * | 8/1995 | Mikhail ......................... 623/23 |
| 5,665,121 A | | 9/1997 | Gie et al. |
| 5,755,720 A | | 5/1998 | Mikhail |
| 5,788,704 A | | 8/1998 | Timperley |
| 6,217,583 B1 | | 4/2001 | Storer |

FOREIGN PATENT DOCUMENTS

DE 196 05 735 A1 6/1997

\* cited by examiner

Primary Examiner—Eduardo C. Robert
(74) Attorney, Agent, or Firm—Lerner, David, Littenberg, Krumholz & Mentlik, LLP

(57) ABSTRACT

A prosthetic implant cement deflector is provided for use in prosthetic surgery when employing an implant in the form of a cannulated phantom or trial prosthesis in combination with a cannulated or cannulated surgical prosthesis or a cannulated prosthesis without a phantom prosthesis. Each cannulated phantom prosthesis or cannulated prosthesis has an insert portion for location in a bone canal and a cannulation bore extending through the insert portion to receive a guide wire. The phantom includes at least one cement deflector element adapted to slide in sealing engagement on the guide wire and which can act to seal the interface between the guide wire and the surface of the distal end of the cannulation bore. The sheath used with the implant has a preformed unperforated sheath adapted to extend over the insert portion of the implant from its distal end to a position at or adjacent to its proximal end.

15 Claims, 4 Drawing Sheets

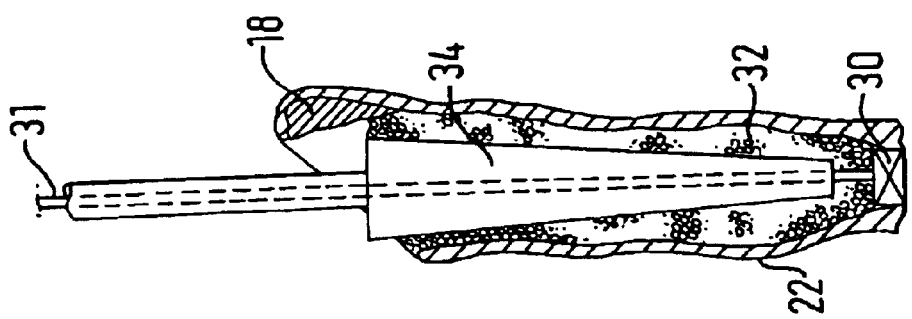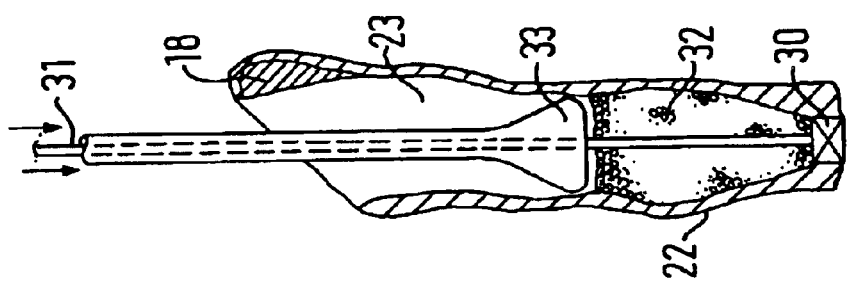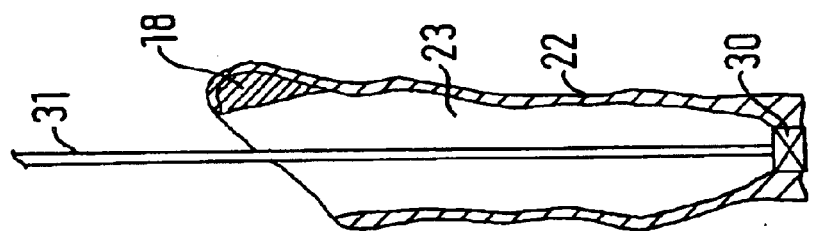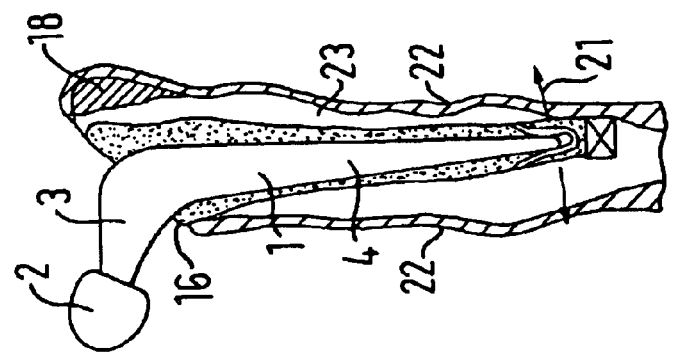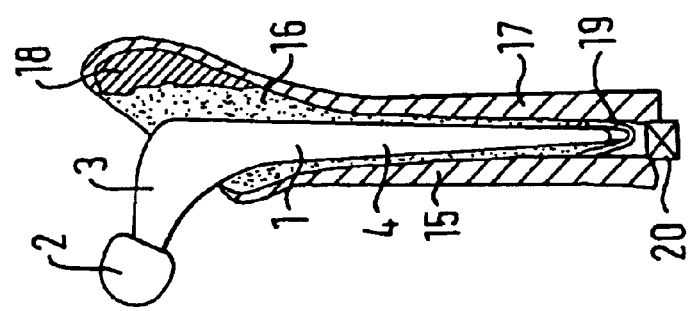

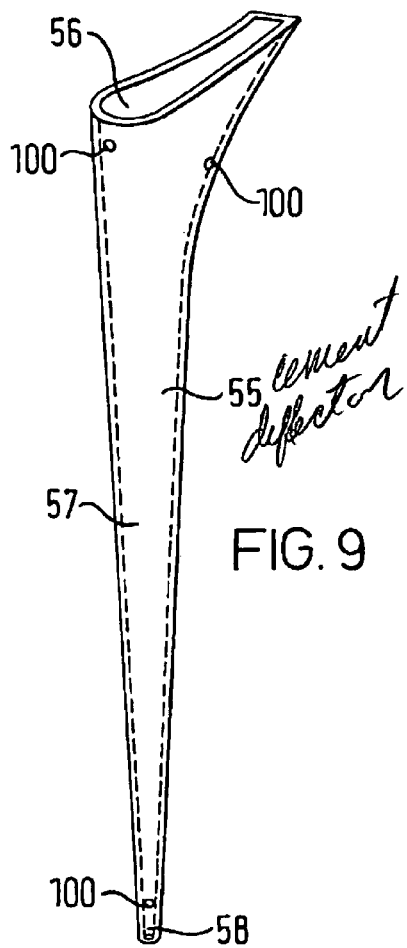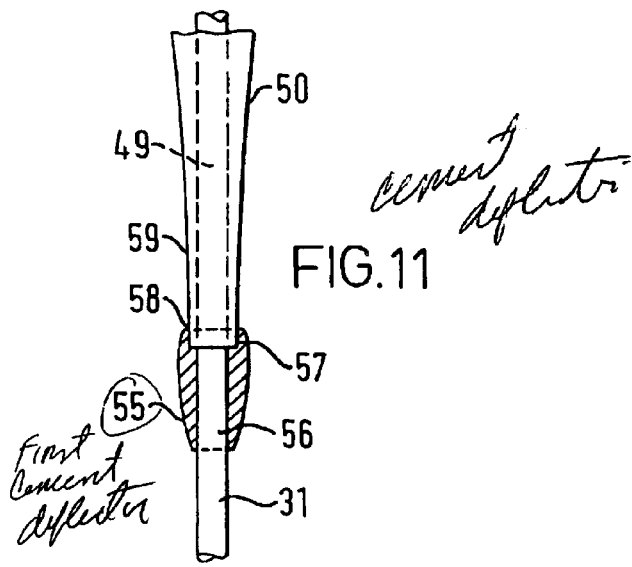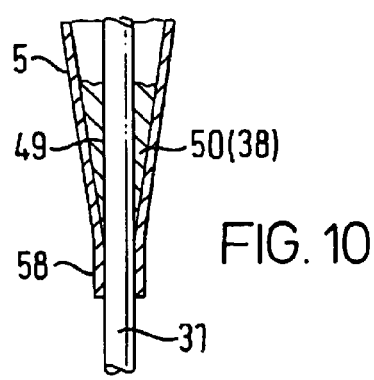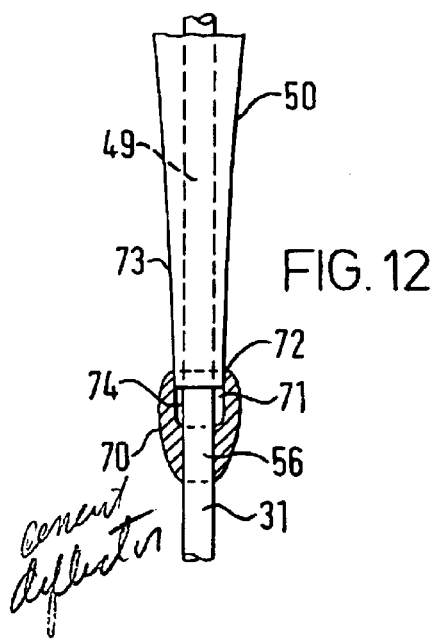

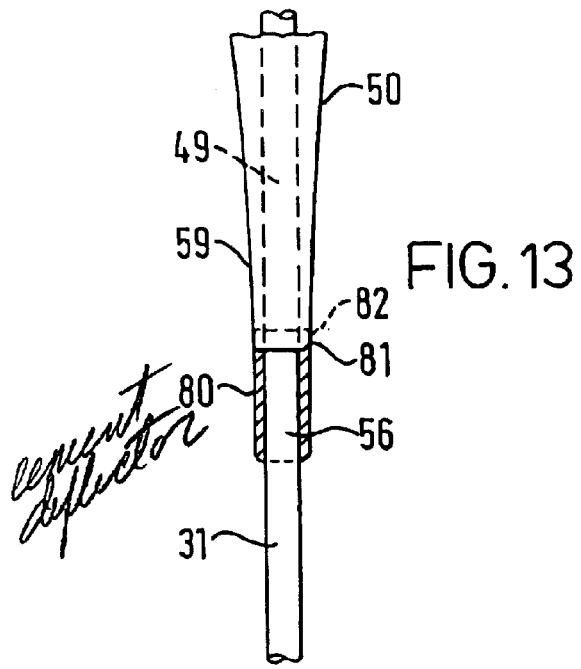
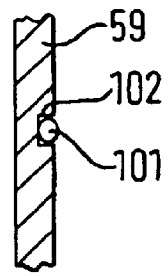
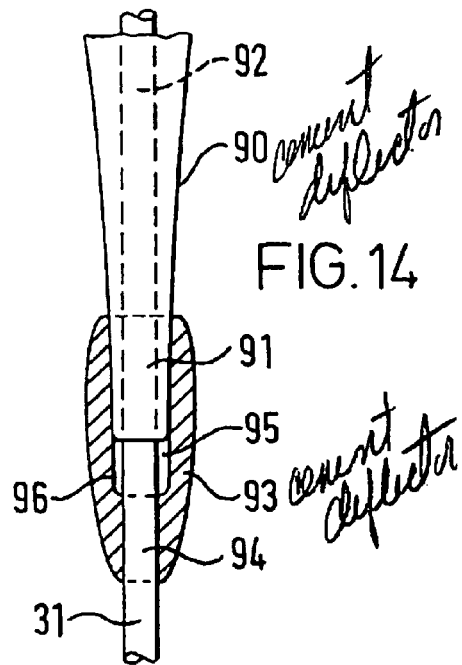
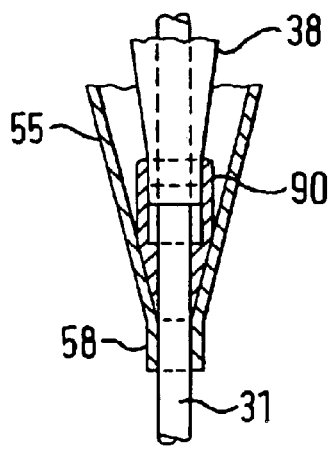

PROSTHETIC IMPLANT CEMENT DEFLECTOR AND METHOD OF IMPLANTATION

BACKGROUND OF THE INVENTION

This invention relates to a prosthetic implant cement deflector and to a set or kit of components to carry out a prosthetic implantation employing such a deflector. The instruments are for use in prosthetic surgery when employing a cannulated phantom or trial prosthesis or a cannulated surgical prosthesis which utilizes a guide wire.

U.S. Pat. No. 6,217,583 shows a prosthetic implant cement deflector for use in prosthetic surgery when employing a cannulated phantom prosthesis and/or a prosthesis which has an insert portion and a bore adapted to receive a guide wire, and comprising a cement deflector element adapted to slide on the guide wire and which can act to seal the interface between the guide wire and the surface of the distal end of the bore. A phantom component is made larger than the actual implant so that a larger cavity is formed to provide a cement mantle of uniform thickness.

The present invention is a development from this concept and has a construction which provides additional advantages in as much that it can help to speed the surgeon's operating time and is easier to handle.

U.S. Pat. No. 5,788,704, the teachings of which are incorporated herein by reference, shows a method and apparatus for implanting a prosthesis. The invention related to a method of guaranteeing the position and thickness of an adequate cement mantle around the cemented implant and shows the use of a phantom component having a tapered insert portion. The phantom component is first inserted into a cavity which has been filled with bone chips which compress. A lining of cement is now applied to the cavity and a cannulated phantom is introduced into the opening.

The phantom is subsequently withdrawn from the cavity, the cement cavity inspected and the surgical prosthesis is finally implanted.

It has been found that using this technique can sometimes cause difficulties due to the passage of cement into the bore of the phantom within the gap between the phantom and the guide wire. Means to prevent these problems are disclosed in U.S. Pat. No. 6,217,583 the teachings of which are incorporated herein by reference and, as mentioned above, the present invention is intended to provide even easier operation of the technique and also of the technique of inserting, for example, a cannulated surgical prosthesis without the use of a phantom.

Preformed unperforated sheaths are shown in U.S. Pat. Nos. 5,197,990 and 5,665,121.

SUMMARY OF THE INVENTION

According to the present invention a prosthetic implant cement deflector is provided for use in prosthetic surgery when employing a cannulated phantom prosthesis in combination with a cannulated or uncannulated surgical prosthesis or a cannulated prosthesis without a phantom or trial prosthesis. Each cannulated phantom prosthesis or cannulated prosthesis has an insert portion for location in the bone and a cannulation bore extending through the insert portion to receive a guide wire. The phantom includes a cement deflector element adapted to slide in sealing engagement on the guide wire and which can act to seal the interface between the guide wire and the surface of the distal end of the cannulation bore. The phantom has a preformed unperforated sheath adapted to extend over the insert portion from its distal end to a position at or adjacent to its proximal end which is at or adjacent the open end of the bone.

Thus, this cement deflector extends not only from a point below the distal tip of the prosthesis insert portion but over all its length within the bone when placed in position.

When the phantom is removed from the guide wire a smooth inner surface is provided by the extended sides of the deflector which are adapted to receive cement and when a cannulated or uncannulated prosthesis is inserted it provides a good fit.

There are also advantages when an uncannulated surgical prosthesis is inserted into the sheath after the phantom and guide wire have been removed.

As mentioned above, the cement deflector can also be used with a direct implantation of a surgical prosthesis along a guide wire, again being employed to prevent cement entering the cannulation bore and, if desired, to provide a void to allow the prosthesis to sink further.

The cement deflector element can be made from any convenient material, for example synthetic plastics material in the form of polymethylmethacrylate (PMMA).

Preferably X-ray markers are incorporated in the cement deflector element so that on subsequent X-ray examination any movement of the cement deflector element or relative movement between the element and the cannulated prosthesis within the cement deflector can be identified.

The X-ray markers can be in the form of spherical tantalum beads. Such markers can be used with a rontgen stereographometric analysis (RSA) to measure displacement of the prosthesis. The markers can also be used if X-ray active markers are applied to the bone, in this case to monitor relative positions of the sheath and bone.

The invention also includes a set of components to carry out a prosthetic implantation comprising a cannulated phantom prosthesis having an insert portion for location in a bone. A cannulation bore extends through the insert portion, a guide wire is provided for sliding location in the cannulation bore, and a cement deflector element is adapted for sliding engagement on the guide wire. The deflector acts to seal the inter face between the guide wire and the distal end of the cannulation bore and in the form of a preformed unperforated sheath which extends over the insert portion from its distal end to a position at or adjacent to its proximal end.

The set or kit of components can also include an uncannulated prosthesis having an insert portion which is shaped and dimensioned to fit into said sheath together with a layer of cement to replace the cannulated phantom prosthesis and guide wire plus a centralizer with a void to allow the prosthesis to sink further in the cured bone cement during extended use.

In an alternative embodiment a cannulated surgical prosthesis can be included having an insert portion and a cannulation bore and having a cement deflector and which, on removal of the cannulated phantom prosthesis from said sheath is adapted to replace it on the guide wire. The cement deflector slidably engages the guide wire and seals the interface between the guide wire and the distal end of the cannulation bore in the prosthesis. The insert portion thereon being shaped and dimensioned to fit into the sheath together with a layer of cement to replace the shallow prosthesis.

The cement deflector can be adapted to be secured to the distal tip of the portion of the cannulated prosthesis and it can be arranged to extend over at least part of the distal tip.

BRIEF DESCRIPTION OF THE DRAWINGS

The invention can be performed in various ways and some embodiment will now be described by way of example and with reference to the accompanying drawings in which:

FIG. 1 is a diagrammatic cross-section showing installation of a total hip prosthesis of known kind in a femur;

FIGS. 2 to 8 are part cross-sectional side elevations showing how a hip prosthesis of the kind shown in FIG. 1 can come loose and be replaced by the method described in U.S. Pat. No. 5,788,704 but employing the present invention;

FIG. 9 is a diagrammatic isometric view of a cement deflector according to the invention;

FIG. 10 is an enlarged cross-sectional view of the distal end of a phantom prosthesis or surgical prosthesis in position on a guide wire with a cement deflector of the type shown in FIG. 9 in place;

FIG. 11 is an enlarged view of a cement deflector as employed by the cannulated surgical prosthesis shown in FIG. 8;

FIG. 12 is a similar view to FIG. 11 of an alternative embodiment;

FIG. 13 is a side view similar to FIGS. 11 and 12 of another alternative embodiment;

FIG. 14 shows a further embodiment which may be used on a cannulated surgical prosthesis of the kind shown in FIG. 8;

FIG. 15 shows how an x-ray marker can be incorporated in a wall of the cement deflector; and FIG. 16 shows how a cement deflector of the kind shown in FIG. 11 is lodged in a cement deflector of the kind shown in FIG. 9.

DETAILED DESCRIPTION

Figure 6:
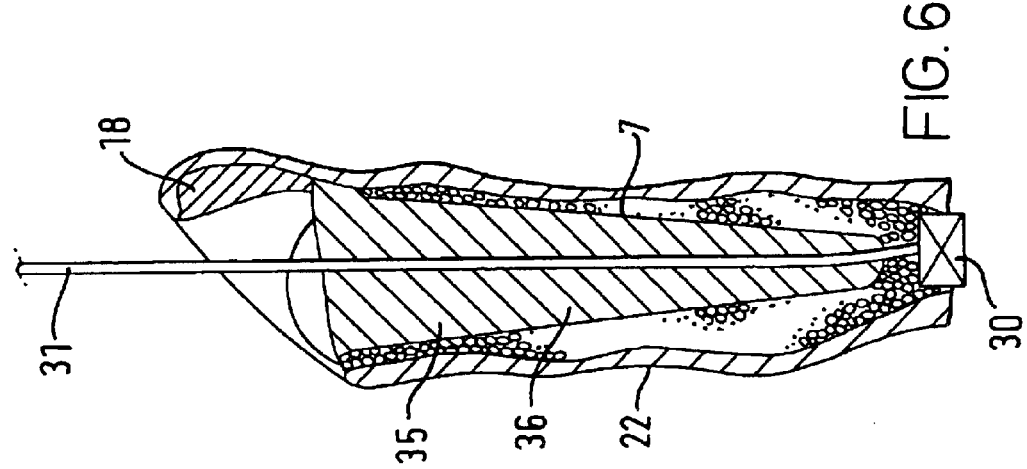

FIG. 1 shows an idealized prior art primary hip intramedullary femoral prosthesis 1 of the straight tapering collarless polished design concept located in a femur 15. The prosthesis has a head 2, neck 3 and stem 4 and is held in place by bone cement indicated by reference numeral 16. The cortical bone 17 of the femur 15 retains some cancellous bone 18. The stem 4 is centralized in the canal by a centralizer 19 of known type and the canal is plugged by a bone plug 20.

FIG. 2 illustrates what can happen when an implant, as shown in FIG. 1, fails. The stem 4 together with the cement 16 breaks away from the bone and a pendulum effect is produced as shown by arrows 21. This causes severe damage within the bone so that all that is left is a thick cortex 22. A space 23 is created which becomes filled by fluids and fibrous tissues.

U.S. Pat. No. 5,665,121, the teachings of which are incorporated herein by reference, shows an implant and a method by which the damaged joint can be repaired and this method will now be described further showing how it can be used in the present invention. The revision procedure commences as shown in FIG. 3 by removing the implant complete with cement and the fibrous tissue by first fitting a bone plug 30 and guide wire 31. Bone chips 32 are now added and compressed using an impactor or ram 33. The bone chips are built up layer by layer in the manner described in U.S. Pat. No. 5,665,121 and a stem phantom 34 is then introduced as shown in FIG. 5 to readily compress the bone chips and form a cavity 35 which is most clearly shown in FIG. 6.

Figure 7:
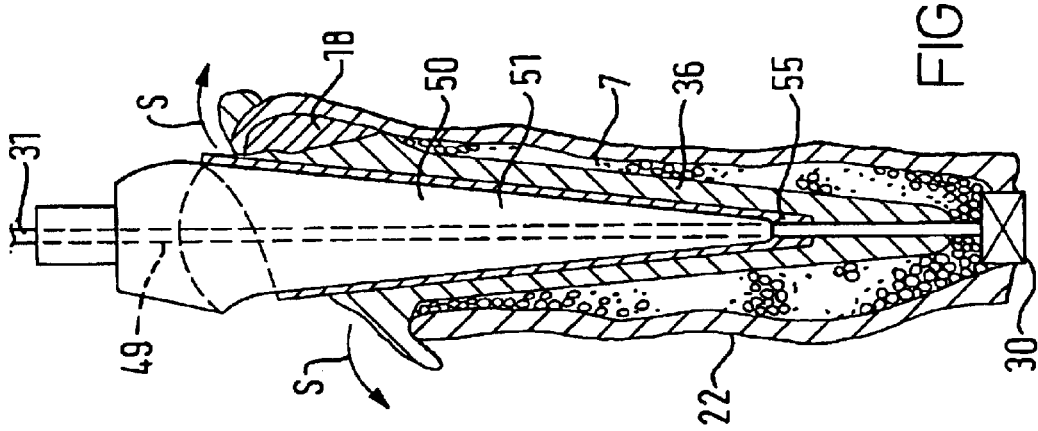

Cavity 35 is now filled with cement 36, as shown in FIG. 6, and this may be pressurized if desired. A cannulated phantom or trial prosthesis 50 having a bore 49 is now introduced into cavity 35, as shown in FIG. 7. The insert portion or stem 51 has dimensions which are identical to or larger than those of a prosthesis which is intended to be fitted. Guide wire 31 provides a means for accurately locating the phantom 50 in place. Unwanted cement from the filling 36 spills out as indicated by the arrow S.

FIG. 7 also shows that, in the preferred embodiment of the present invention, a prosthetic implant cement deflector 55 is provided which is in the form of a sheath and shown more clearly in FIG. 9 and 10. Prior to placing phantom 50 on guide wire 31 cement deflector 55 is placed on the phantom and moves down guide wire 31 with it when the phantom is introduced into the opening. Because of the material from which the deflector is made it acts to seal the interface between the wire 31 and the surface of the bore 49 in the phantom. Deflector 55 can however slide down wire 31.

Figure 8:
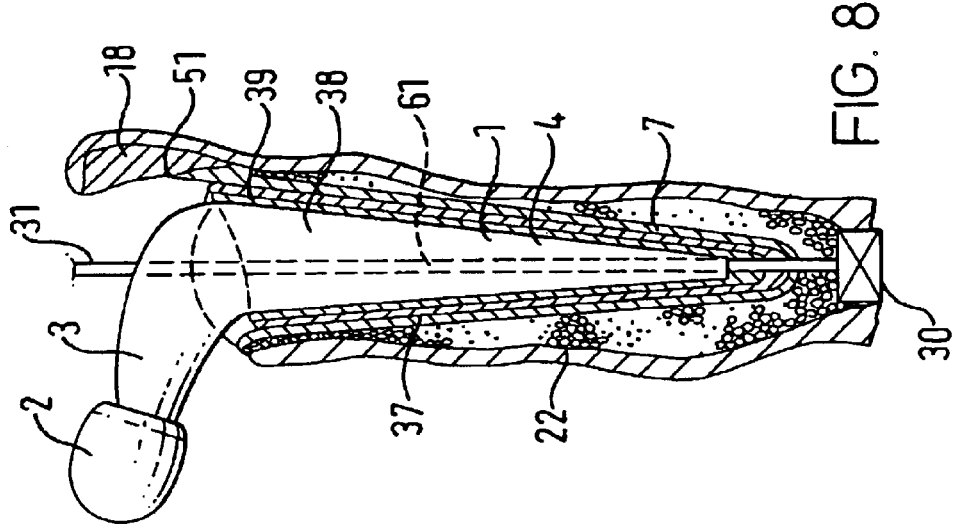

Once the cement is cured or in a suitable state phantom 50 is withdrawn from the cavity leaving cement deflector 55 in place and forming a lining of cement 37 as shown in FIG. 8. Because the deflector has acted to prevent cement from entering the interface between wire 31 and bore 49 the phantom can be withdrawn without difficulty. To further assist withdrawal, phantom 50 will generally have a polished surface, or alternatively, be coated with a material which does not adhere to the sheath of cement deflector 55.

Guide wire 31 is left in place and a further quantity of cement 39 is introduced into the cavity formed by the walls of deflector sheath 55. A cannulated prosthesis 38 is then introduced down guide wire 31. This prosthesis having an insert portion in the form of a stem, a neck 3 and head 2.

Prior to insertion of the cannulated prosthesis 38 a second cement deflector is fitted to its distal tip, this deflector being of the kind shown in FIGS. 11 to 14 and being the subject of U.S. Pat. No. 6,217,583. The embodiment of this type of deflector is described below and in FIG. 8. A deflector of the type shown in FIG. 14 is utilized. Prior to placing cannulated prosthesis 38 on guide wire 31 the second cement deflector, indicated by reference numeral 90, is placed on guide wire 31. The wire is then engaged onto the distal tip of prosthesis 38 which moves down guide wire 31 and together with the second deflector 90 is introduced into the opening. Because of the material from which the deflector 90 is made it acts to seal the interface between wire 31 and the surface of the bore in the cannulated prosthesis. As cement deflector 90 approaches the distal end of the opening in the first cement deflector 55 prosthesis 38 and second deflector 90 lodges in the deflector 55 as shown in FIG. 16.

Once the cement is cured or in a suitable state, the guide wire is unthreaded from the intramedullary plug 30 and withdrawn through the deflectors and prosthesis 38.

If desired the length of the stem of prosthesis 38 can be arranged so that a void (not shown in FIG. 8) is provided between the proximal end of the distal part of deflector 55 and the distal end of the second deflector 90. This void allows prosthesis 38 to sink further into the cement after curing as required and as is well known when using stems of this type.

Again, if desired, the first cement deflector 55 and/or the second cement deflector 98 can be provided with means, for example wings (now shown, so that it acts as a centralizer. The centralizer thus provided can also be shaped to provide the void between the second centralizer 90 and the upper part of the distal end of the centralizer 55 to accommodate subsequent downward movement. This centralizer will of course be inserted with prosthesis 38.

In an alternative arrangement cannulated prosthesis 38 can be replaced by an uncannulated prosthesis. The technique of insertion of this uncannulated prosthesis is similar to that described above but, prior to insertion, guide wide 31 is unscrewed from intramedullary plug 30 and removed. The second cement deflector is therefore not required because no guide wire is employed but a centralizer of the kind referred to above, may be shaped to have a void into which the uncannulated prosthesis can sink further. The choice of whether to employ a cannulated or uncannulated prosthesis will depend upon the requirements of the surgeon at the time of the operation.

The stem geometry must allow an appropriate mechanism for the transmission of the load between the stem and the cement mantle so formed and an ideal hip stem for the use of this technique is of the type which incorporates a double tapered and polished stem form which effectively engages the cement mantle causing principally compressive transmission of load from the stem to the cement and thereby to the bone.

This selection is important if the surgeon chooses to use the original cement mantle formed by the phantom 50 with the definitive implanted stem. Inevitably manufacturing variations will result in a marginal mismatch between the mantle and the definitive stem. The use of the double tapered stem which allows tapered re-engagement to occur with the relatively compliant and visco-elastic cement at body temperature results in the effective taper load transmission despite the manufacturing differences.

With existing techniques there can be inappropriate positioning of an implant within the cavity in the bone and they do not result in a uniform control thickness of cement mantle which would give a better mechanical performance of the cement. This is a particular advantage of the new method of insertion.

This method can also be used with a cannulated system of broaches for shaping the opening. They can be used to form a known cavity shape over and above the nominal size of the implant and further guarantees the mantle geometry.

A system of depth indicators can be used for example as shown in the technique described in U.S. Pat. No. 5,192,283 and the depth indication system could also be used to position the phantom insert within the cavity formed by such broaches.

FIGS. 9 and 10 show a typical example of the present invention in more detail and which is for use in the manner shown in FIGS. 7 and 8. The preferred cement deflector 55 is made from polymethylmethacrylate (PMMA) and is provided with a hollow tapering bore 56 and has side walls indicated by reference numeral 57. The distal end 58 is in the form of a substantially circular tube which is of slightly less diameter than the guide wire 31 with which it is to be used. The overall dimensions of the deflector are such that they are adapted to extend over the insert portion, that is the stem of the phantom prosthesis or prosthesis with which it is to be used from its distal end to a position at or adjacent its proximal end and therefore acts as a sheath. The dimensions will clearly be seen from FIGS. 5, 7 and 8. The sheath is preformed and is unperforated throughout its length.

FIG. 10 shows how the preferred distal end 58 of the sheath distorts to accommodate the guide wire 31 and therefore acts as a close sealing fit on the wire. The sheath walls 57 closely engage the walls of the phantom prosthesis 50 or prosthesis 38 to provide the seal between the interface between guide wire 31 and the distal end of cannulation bore 49 in the phantom prosthesis or surgical (final) prosthesis.

FIGS. 11 to 14 show examples of second cement deflectors which can be used on a cannulated surgical prosthesis which are to be engaged within the sheath provided by first cement deflector 55 and which can be employed in the arrangement shown in FIG. 8.

Referring to FIG. 11 there is shown a first embodiment of the second cement deflector of the present invention. The cement deflector 60 is made from polymethylmethacrylate (PMMA) and is provided with a central bore 61 which is dimensioned to be a sliding fit on guide wire 31. The proximal end 62 of the deflector is recessed at 63 to provide a push or press fit onto the distal end 64 of cannulated prosthesis 38.

The primary advantage of the cement deflector is that when the phantom prosthesis or prosthesis is moved down the guide wire 31 cement deflector 60 acts to prevent cement passing into the guide bore of the prosthesis around guide wire 31. If the technique described with regard to FIG. 8 is employed without such a cement deflector, cement may pass up guide wire 31 into the bore, and if the prosthesis is left in the opening until the cement part solidifies, it can be difficult to withdraw the guide wire due to the ingress of cement.

FIG. 12 shows an alternative embodiment in which the same reference numerals are used to define similar parts but in this construction the deflector 70 is provided with an extended, recess 71 the proximal end 72 of which is shaped and adapted, for example by being tapered, to engage the distal end 73 of the cannulated prosthesis 38. This construction is designed so that the distal end of the prosthesis 38 can extend into the proximal end 72 of the recess of the deflector 70 and a void 74 is provided by the lower part of the recess 71 into which the prosthesis 38 can subsequently sink. Thus, this construction, as shown in FIG. 12, can be used to replace the construction shown in FIG. 11 when used in the surgery described with regard to FIGS. 7 and 8 and overcomes the requirement for a centralizer.

FIG. 13 shows another alternative embodiment in which the same reference numerals are used to indicate similar parts to those shown in FIG. 11. In this construction however the cement deflector 80 has an external diameter which is substantially the same as external diameter of distal end 59 of prosthesis 38. The distal end of the prosthesis 38 is recessed as indicated by reference numeral 81 and receives a flange 82 formed on the end of the deflector. Thus, with this construction the deflector is held in place by the flange 82 during insertion and acts in similar manner to the inserter described and shown in FIG. 11.

FIG. 14 shows a further embodiment of cement deflector 90 which can be used with a cannulated prosthesis. The same reference numerals are again used to describe similar parts to those shown in the previous figures. Prosthesis 38 has a distal end 91 and a bore 92 to receive guide wire 31. A cement deflector 93 is employed which has a bore 94 to receive the guide wire 31 and an enlarged bore 95 which is dimensioned to receive the distal end of prosthesis 38, for example by being tapered.

This embodiment can be used either on the insertion into a newly prepared cavity in a bone or when used for replacement surgery.

The proximal portion of enlarged bore 95 provides a void 96 in which prosthesis 38 can subsequently sink. Once the prosthesis has been placed in position and the cement has set guide wire 31 is of course removed but the cement deflector will once again have acted to prevent cement entering the interface between the wall of bore 92 and wire 31 thus allowing removal of guide wire 31 without the usual difficulties.

Preferably cement deflector 55, as shown in FIGS. 9 and 10, is provided with three x-ray markers, two at the upper end on the lateral and medial faces and a third at distal end 58. Each of the markers is in the form of a suitable radio-opaque bead 101 made, for example, from tantalum. Each bead is a press-fit in a recess 102 in the sheath wall 59.

The x-ray markers can be used for rontgen stereographometric analysis (RSA) and to indicate if there is any relative movement between the sheath and the prosthesis and, provided x-ray markers are also located in the bone, to show any relative movement between the sheath and the bone.

If desired, similar markers can be incorporated in the walls of the cement deflectors shown in FIGS. 11 to 14.

Although in the present description a technique as set forth in U.S. Pat. No. 5,665,121 is described the invention can equally be applied to a newly made cavity in a femur.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A kit of components to carry out the implantation of a prosthetic implant comprising a cannulated phantom prosthesis having an insert portion for location in a bone, a cannulation bore extending through said insert portion, a guide wire for sliding location in said cannulation bore, and a first cement deflector element adapted for sliding engagement on said guide wire, said deflector acting to seal the interface between the guide wire and the distal end of the cannulation bore, said first deflector being a preformed unperforated sheath which extends over the insert portion of said phantom prosthesis from its distal end to a position at or adjacent to its proximal end and a cannulated prosthetic implant having an insert portion and a cannulation bore and a second cement deflector which, on removal of said cannulated phantom prosthesis from said first cement deflector, said second cement deflector may be placed on said guide wire, said second cement deflector slidably engaging said guide wire and sealing the interface between the guide wire and the distal end of the cannulation bore in said prosthetic implant, and said insert portion thereon being shaped and dimensioned to fit into said sheath of said first cement deflector together with a layer of cement.

2. The kit as set forth in claim 1 wherein the first cement deflector is made from synthetic plastics material.

3. The kit as set forth in claim 2 wherein the synthetic plastics material is polymethylmethacrylate (PMMA).

4. The kit as set forth in claim 2 wherein X-ray markers are incorporated in the first cement deflector element.

5. The kit as set forth in claim 4 wherein the X-ray markers are in the form of spherical tantalum beads.

6. The kit of components as claimed in claim 1 wherein said first cement deflector can be adapted to be secured to a distal end portion of the cannulated phantom prosthesis.

7. The kit of components as claimed in claim 6 wherein said second cement deflector extends over at least part of a distal end of the cannulated prosthetic implant.

8. A kit for implanting a prosthetic femoral component in a femur comprising:
   a plurality of trial femoral prosthesis having a cannulation bore extending therethrough;
   a guide wire for being received within said bore;
   a first cement deflector for sliding engagement with the guide wire, said deflector having a cavity for receiving said trail femoral prosthesis and a leading end acting to seal the interface between the guide wire and the distal end of the cannulation bore in said trial prosthesis;
   a prosthetic femoral component including a stem portion with a distal tip and having a cannulation bore for receiving a guide wire; and
   a second cement deflector having a first end with a recess for receiving the distal tip of said prosthetic femoral component and a bore therethrough for receiving said guide wire.

9. The kit as set forth in claim 8 wherein said second deflector is sized to be received within the cavity of said first cement deflector.

10. The kit as set forth in claim 8 wherein said recess in said second cement deflector has a first proximal portion for receiving said prosthesis tip and a second distal portion for allowing said tip to sink further into the second deflector after implantation.

11. The kit as set forth in claim 8 wherein the first cement deflector is made from synthetic plastics material.

12. The kit of components as set forth in claim 8 wherein said second cement deflector can be adapted to be secured to the distal end portion of the cannulated prosthesis.

13. The kit as set forth in claim 8 wherein the synthetic plastics material is polymethylinethacrylate (PMMA).

14. The kit as set forth in claim 8 wherein X-ray markers are incorporated in the first cement deflector element.

15. The kit as set forth in claim 14 wherein the X-ray markers are in the form of spherical tantalum beads.

* * * * *